(12) United States Patent
Gil

(10) Patent No.: US 9,174,248 B2
(45) Date of Patent: Nov. 3, 2015

(54) DEVICE FOR CLEANING A HEARING AID

(75) Inventor: José Antonio Gil, St. Bauzille de Montmel (FR)

(73) Assignee: MG DEVELOPMENT, Perols (FR)

( * ) Notice: Subject to any disclaimer, the term of this patent is extended or adjusted under 35 U.S.C. 154(b) by 162 days.

(21) Appl. No.: 13/879,372

(22) PCT Filed: Oct. 13, 2011

(86) PCT No.: PCT/FR2011/052389
§ 371 (c)(1),
(2), (4) Date: Apr. 30, 2013

(87) PCT Pub. No.: WO2012/049429
PCT Pub. Date: Apr. 19, 2012

(65) Prior Publication Data
US 2013/0220385 A1    Aug. 29, 2013

(30) Foreign Application Priority Data

Oct. 13, 2010 (FR) ...................... 10 58349

(51) Int. Cl.
| | |
|---|---|
| *H04R 25/00* | (2006.01) |
| *B08B 3/04* | (2006.01) |
| *A61L 2/18* | (2006.01) |
| *B08B 3/00* | (2006.01) |
| *B08B 3/10* | (2006.01) |
| *B08B 7/00* | (2006.01) |

(52) U.S. Cl.
CPC ... *B08B 3/04* (2013.01); *A61L 2/18* (2013.01); *B08B 3/00* (2013.01); *B08B 3/102* (2013.01); *B08B 7/00* (2013.01); *H04R 25/00* (2013.01); *A61L 2202/24* (2013.01); *H04R 25/654* (2013.01); *H04R 2460/17* (2013.01)

(58) Field of Classification Search
CPC .... B08B 3/04; B08B 2203/007; H04R 25/02; H04R 25/30; H04R 25/505; H04R 2460/17
USPC ........ 134/105, 198, 110, 88, 89, 90, 109, 111
See application file for complete search history.

(56) References Cited

U.S. PATENT DOCUMENTS

| | | | | |
|---|---|---|---|---|
| 5,813,081 | A * | 9/1998 | Wang et al. | 15/210.1 |
| 5,875,800 | A * | 3/1999 | Hulskotte | 134/56 R |
| 2006/0254626 | A1* | 11/2006 | Botts et al. | 134/110 |
| 2008/0128007 | A1* | 6/2008 | Stern | 134/58 R |
| 2008/0253579 | A1* | 10/2008 | Cronin et al. | 381/60 |
| 2009/0071511 | A1* | 3/2009 | Kurokawa et al. | 134/105 |

FOREIGN PATENT DOCUMENTS

| | | |
|---|---|---|
| FR | 2922770 A1 | 5/2009 |
| WO | 2005 125276 A1 | 12/2005 |

* cited by examiner

*Primary Examiner* — Michael Barr
*Assistant Examiner* — Tinsae Ayalew
(74) *Attorney, Agent, or Firm* — Andrew W. Chu; Craft Chu PLLC

(57) ABSTRACT

The device for cleaning at least one medical hearing unit includes an earpiece, and a space for receiving the earpiece, the space having at least one seat receiving the earpiece and an orifice with a cavity underneath. There is a circulator for a liquid within the space to contact the earpiece. The cavity includes an outlet for flow or aspiration of liquid, an opening opposite, and, below each orifice, a directing device to guide the liquid towards and under each orifice, as far as the outlet, in such a way that liquid flows across the earpiece.

12 Claims, 2 Drawing Sheets

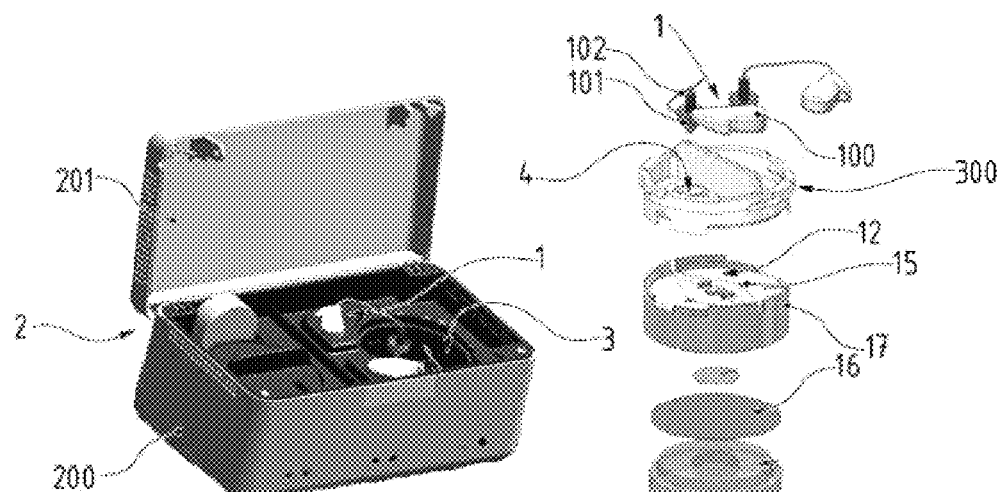
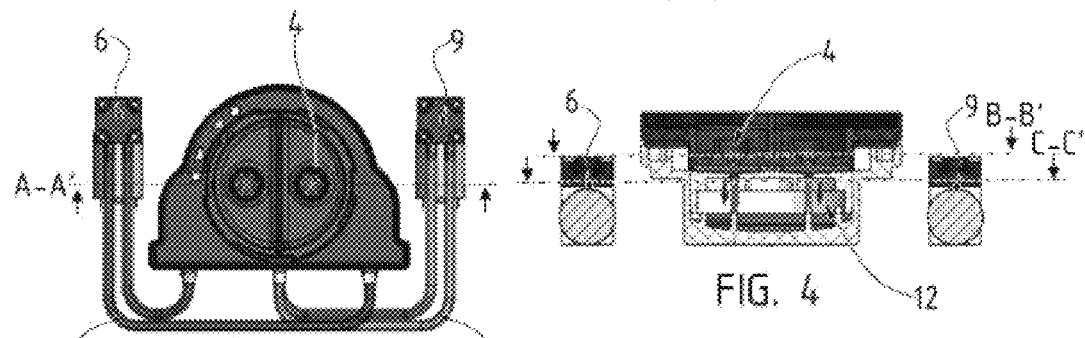
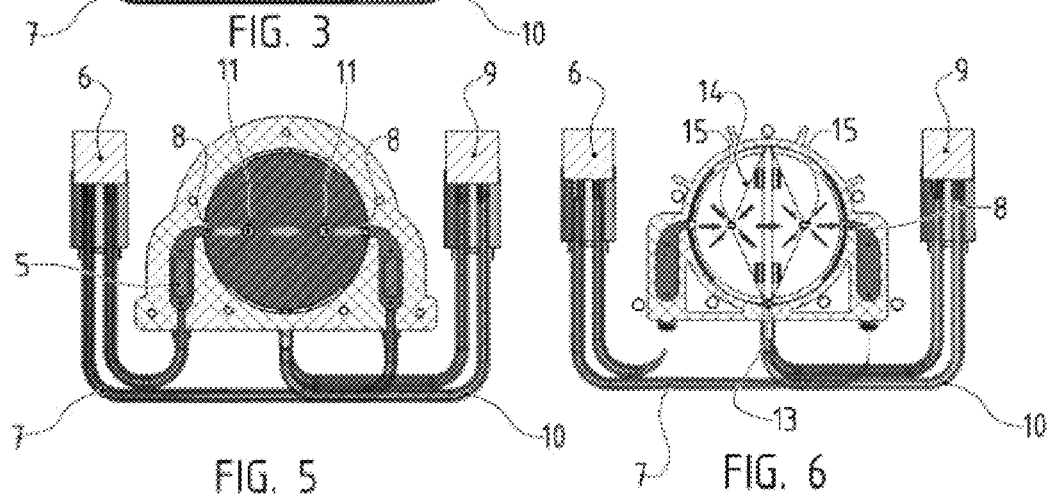

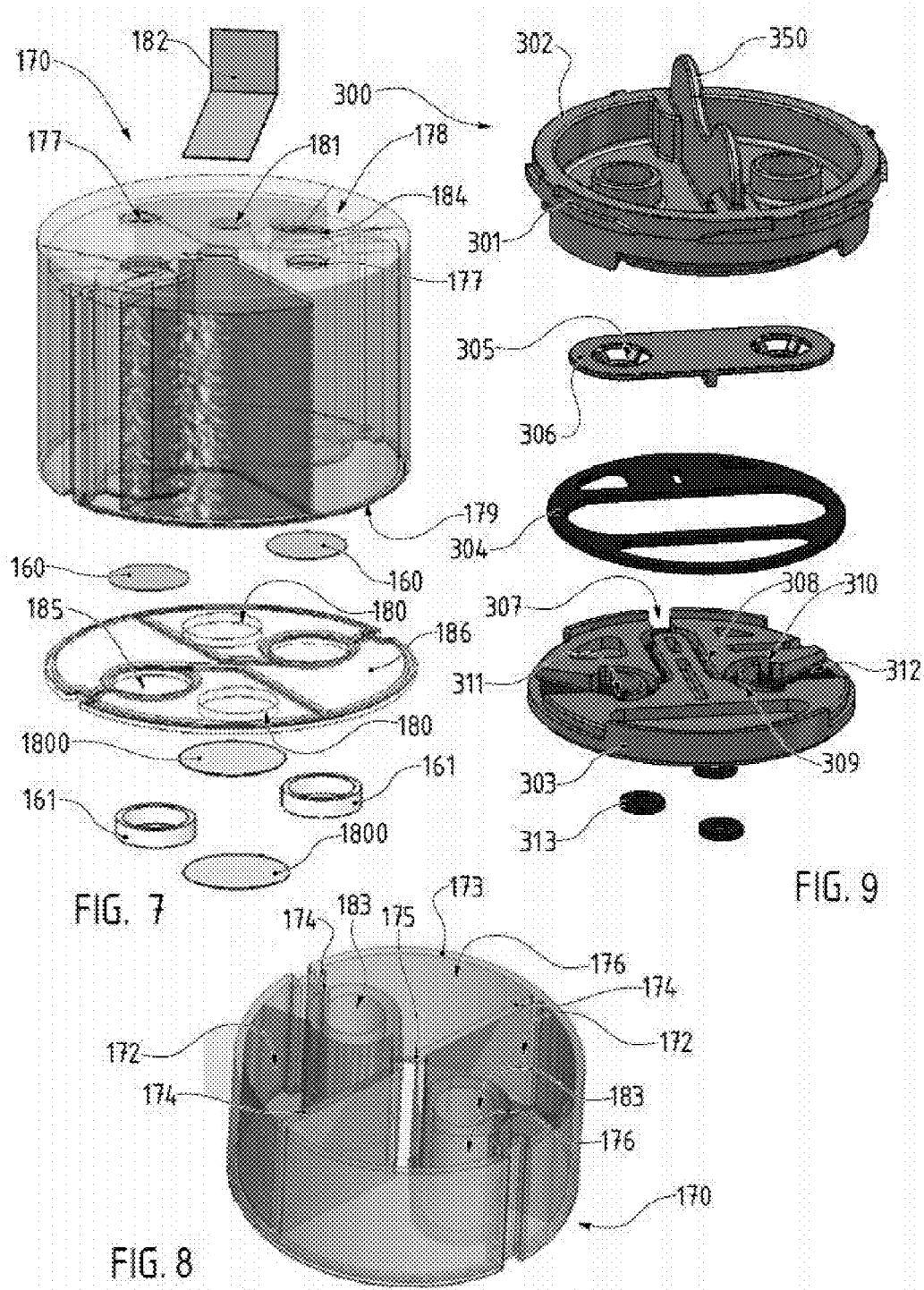

DEVICE FOR CLEANING A HEARING AID

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention is related to the medical field of hearing, in particular to medical hearing devices for persons suffering from hearing losses and hard-of-hearing.

2. Description of Related Art Including Information Disclosed Under 37 CFR 1.97 and 37 CFR 1.98.

In a known way, such devices are generally in the form of a hearing aid that is positioned, hidden and nearly invisible, behind the ear or in the auditory meatus. This aid includes power-supply means in the form of a cell or battery, as well as means for processing the sounds perceived and for transmitting to emitting means, which it is connected to. These emitting means are in the form of a shaped earpiece, which can be made to measure, so as to be inserted into the auditory meatus. Said earpiece permits to emit the processed sounds transmitted from said aid, often while amplifying them.

Because of the insertion of the earpiece in the auditory meatus such hearing aids considerably improve the hearing of the persons wearing a device. However, they have a major drawback related to the direct contact of said earpiece with the ear wax, but also with all the dust, dirt and material particles it conveys along and out of the hearing canal. This results into a reduction of the efficiency of the earpiece and into a degradation of the hearing of the person wearing a device.

More constraining, some aids are deteriorated and returned to the manufacturer in order to be repaired or replaced, thus generating additional costs and times.

That's why the earpiece must be cleaned periodically, in order to eliminate said impurities. But the electronic components integrated in the earpiece prohibit the use of liquid for this cleaning.

A known solution is described in WO 2005/12576 relating to a device for diagnosing and cleaning a hearing aid, in particular its earpiece. Such a device permits an individual to perform at home a diagnosis of his device and to clean it periodically, without using any liquid whatsoever likely to deteriorate the electronic components forming said earpiece. Such a cleaning occurs through drying the ear wax and aspiration of the so dried particles.

To this end, heating means are arranged inside a recess for receiving said earpiece, so as to diffuse sufficient heat inside this space to dry the ear wax. These heating means are in the form of resistors or of ultraviolet radiation sources. A ventilator is added, in order to ensure a flow of the so heated air, namely in the earpiece. Therefore, the moisture content present in the ear wax is reduced until it permits the aspiration of the dried residues by a vacuum pump and their evacuation to a storage tank.

Such a cleaning device has a major drawback related to the drying of the ear wax. Indeed, though most of the dried particles are aspired by the vacuum pump, part of the residues remains, often stuck in the indentations of the earpiece.

A similar device is described in WO 98/4885, using a putting into circulation of hot air by blowing and aspiration.

Another solution has been devised through WO 2007/005748, which describes a device for cleaning hearing aids through centrifugation. In fact, said aids are placed in a compartment driven in rotation until it reaches such a speed as to subject said aids to a force in the range between 200 and 400 G. At this speed, the ear-wax particles are ejected and aspired. Ultrasound waves can also facilitate the loosing of the ear-wax particles during the centrifugation. It is thus possible to heat the enclosure between 41 and 60 degrees Celsius, so as to dry the ear wax and once again to facilitate its loosing.

According to a specific embodiment, the aid is immersed into a cleaning liquid, also put into rotation, then dried by an additional centrifugation step. However, the electronic components contained in the aid are very sensitive to moisture, so that the immersion into a liquid can cause a deterioration.

Another solution is known from US 2008/128007, which describes a device for cleaning and recharging a hearing aid. In particular, this cleaning occurs by means of a fluid, put into circulation from a chamber, until it is brought into contact with said earpiece.

In this respect, the earpiece is positioned in a recess having a complementary shape and the inner wall of which ensures a <<grip>> so as to maintain it in position, In addition, the earpiece, positioned in said recess, is arranged so that a portion of said earpiece extends downwardly through the wall of the recess. Once it has been positioned, the cleaning fluid fills the cavity located under the recess, so as to immerge only said protruding portion.

Though such a solution permits to target the cleaning at the level of the end of the ear mold of the earpiece, no evacuation or aspiration of the fluid is provided in the lower cavity during the cleaning, leaving the ear mold immersed, which results from a cleaning that is little satisfactory, longer because of the mere immersion and likely to damage the electronic components.

The aim of the invention is to cope with the drawbacks of the state of the art by providing a device for cleaning a medical hearing device, in particular its earpiece, formed of an ear mold shaped so as to be inserted into a person's auditory meatus, through liquefaction of the ear wax, then its aspiration.

SUMMARY OF THE INVENTION

To this end, such a cleaning device provides to humidify the ear wax, in order to permit its complete liquefaction.

Advantageously, the humidification according to the invention is localized at the level of the ear molds shaped so as to be inserted into the auditory meatus, without entering into contact with the rest of the aid. In fact, a liquid laps against these ear molds, without the latter remaining into immersed contact and, hence, without risk of deteriorating the electronics of the earpiece and said aid.

To this end, the cleaning device according to the invention comprises, on the one hand, a space for receiving said earpiece, said space comprising at least one recess shaped so as to receive said ear mold, said recess comprising in the lower portion an orifice shaped so that the distal end of said ear mold protrudes into a cavity provided for under said recess and, on the other hand, means for putting into circulation in said space a liquid so that the latter enters into contact with said ear mold, said means for putting into circulation said liquid ending in said cavity in the form of at least one pipe, wherein said cavity comprises at least one outlet for the flowing or aspiration of said liquid, ending in front under each orifice, and in that the bottom of said cavity comprises means for directing said liquid towards and under said orifice, until said outlet, so that said liquid laps against said distal end.

Another advantage of the present invention resides in the possibility of using a disinfecting liquid.

Therefore, the heating introduced in the invention is only aimed at drying the portion of the aid that has been cleaned by humidification.

According to other additional features, corresponding to particular embodiments, said directing means are in the form of protrusions, veins or grooves.

Preferably, said device comprises means for heating said space through putting into circulation of heated air.

In particular, such a device may comprise filtering means located in the lower portion under said cavity.

Furthermore, said filtering means are in the form of a permeable membrane formed of fibers, foam or of a woven material the separation of which permits to recover the ear wax particles, whether liquefied or not, as well as the dust and dirt, while letting pass the liquid.

According to a specific embodiment, the device comprises a cartridge with a cylindrical shape inserted in said space, said cartridge being subdivided internally into several storage and recycling compartments delimited by the peripheral wall of said cylinder and radial walls.

According to a particular embodiment, said storage compartments comprise orifices provided for in the lower face and closed by protection caps, as well as holes provided for in the upper face, and said recycling compartments comprise two recycling orifices provided for in the upper face of said cartridge.

Preferably, said cartridge comprises two central channels with a cylindrical shape passing internally through said cylinder from the upper face to the lower face and ending outside at the level reciprocally of upper holes provided for in the upper face and of lower holes provided for in the lower face.

In particular, said device comprises a dome having a cross-section complementary to that of the cross-section of the space, so as to insert into same in the upper portion and, after insertion, said dome being mounted movable in rotation according to the central axis of said space, so as to rotate clockwise, or inversely, into several operation positions.

In addition, said dome comprises an upper portion and a lower portion, the latter being hollow so as to provide in same for grooves inside which the fluid will flow during the cleaning, an opening being provided for at the periphery and connected to a bifurcation connecting two symmetrical grooves each ending in front of a wall having the shape of an arc of a circle biasing the fluid on both sides during its circulation until the level of each end of each wall towards a stop made at right angles biasing the fluid to the outside.

Further features and advantages of the invention will become clear from the following detailed description of the non-restrictive embodiments of the invention, with reference to the attached figures.

BRIEF DESCRIPTION OF THE DRAWINGS

FIG 1 represents a perspective view of the cleaning device in open position, with two aids placed inside.

FIG 2 is an exploded perspective view of a detail of said device with two aids.

FIG 3 is a top plan view from above.

FIG 4 is a cross-sectional view according to the vertical plane A-A' of FIG 3.

FIG 5 is a cross-sectional view according to the horizontal plane B-B' of FIG 4.

FIG 6 is a cross-sectional view according to the horizontal plane C-C' of FIG 4.

FIG 7 is an exploded perspective representation of a cartridge for recharging the device according to the invention.

FIG 8 is a perspective view according a horizontal cross-sectional plane of such a cartridge.

FIG 9 is an exploded perspective view of another detail of the invention.

DETAILED DESCRIPTION OF THE DRAWINGS

The present invention relates to the cleaning of a medical hearing device 1, namely a hearing aid.

Such an aid comprises a casing 100 shaped so as to be placed behind the ear and connected by a wire 102, or not, to an earpiece 101 in the form of an ear mold or <<dome>> shaped so as to be inserted into the auditory meatus of the person wearing the device. Such an ear mold can be a naked earpiece 101 the end of which is covered with a standard flange for insertion and maintaining in the auditory meatus, or directly shaped to measure.

Advantageously, the invention relates to a device 2 for cleaning such a medical hearing device 1, in particular the ear mold forming its earpiece 101.

To this end, as visible in FIG 1, the cleaning device 1 according to the invention comprises an enclosure in the form of a box 200 on which a lid 201 is mounted in a hinged way through hinges, so as to pass from an open position to a closed position, and vice-versa.

It should be noted that in closed position, said box 200 can be tight. Namely air tight and/or tight to any fluid or liquid.

Such an enclosure comprises a space 3 for receiving said earpiece 101.

In particular, said space 3 is shaped so as to permit the complete or partial insertion of said earpiece 101.

According to a preferred embodiment, said space 3 comprises at least one recess 4 in which said earpiece 101 can be placed. In particular, said recess 4 is provided for in a closing plate 300. Said space 3, in particular this plate 300 can preferably also comprise two recesses 4, each one aimed at receiving each ear mold of the earpieces 101 of two aids 1. Said plate 300 then serves as a support for the <<dome>>.

Each recess 4 is shaped in a way complementary to said earpiece 101 or is provided for in a flexible and elastic material, such as for example silicone or a cellular or semi-rigid material, possessing elastic characteristics or some resilience, such as foam, permitting its deformation during the insertion of said earpiece 101, its maintaining within the recess 4, as well as the recovery of its shape after extraction of the ear mold of the earpiece 101.

The cleaning of said earpiece 101 occurs through liquefaction of the ear wax, residues, dust or the like.

Advantageously, an essential feature of the present invention resides in humidifying the ear mold of each earpiece 101 during its cleaning, in order to permit the liquefaction of the ear wax and the complete removal of the latter.

In particular, the humidification of the ear mold occurs through putting a fluid into circulation, said fluid entering into contact with said ear mold.

It should be noted that said fluid can be a liquid, such as a solution, namely a cleaning and/or disinfecting liquid.

Moreover, said device comprises means 9 for putting said fluid into circulation in a circuit 10. Said means 9 permit the injection and aspiration of said fluid through said circuit 10 and reciprocally to and from said space 3.

In particular, the injection and aspiration of said fluid occur at the level of each recess 4, so as to lap against a portion of the ear mold of each earpiece 101.

As visible in the embodiment represented in the figures, each recess 4 comprises in its lower portion at least one orifice 11 into which inserts the end of the ear mold of an earpiece 101. Such an orifice 11 thus permits to let protrude under the recess 4 the distal end of said ear mold aimed at inserting as deep as possible into the auditory meatus, and being therefore the dirtiest portion to be cleaned.

The circulation of the cleaning liquid occurs in the underlying portion of said recesses 4. In particular, a cavity 12 is provided for in said space 3, under the recess 4. This cavity 12 is designed tight and permits the injection of the liquid and its flow.

In particular, said liquid is projected through at least one pipe 13 injecting the liquid into said cavity 12. In fact, the circuit 10 is open at the level of the cavity 12. Therefore, the liquid exits and flows at the level of the bottom of the cavity 12, shaped so as to guide the liquid in contact with the portion of the ear mold of each earpiece 101 projecting through said orifice 11. The liquid then laps against this end, without therefore penetrating into the upper portion of the recess 4 and the space 3 located in the upper portion.

Preferably, said bottom can have means 14 permitting to direct the liquid from each pipe 13 to the bottom of the orifices 11. Such directing means 14 can be in the form of projections, namely fins, or in the form of veins, grooves or the like.

Advantageously, the direction, the evacuation and the aspiration ensure that the cavity does not fill with fluid, by forming a kind of vortex, such as a whirl, under the distal end of the earpiece, at the level of the orifice 20 corresponding to the outlet. The fluid then circulates only to clean, without remaining <<stagnant>> in contact with the ear mold.

Once arrived at the level of each orifice 11, the liquid laps against the end of said ear mold inserted in its recess 4, then is aspired by an outlet 15 ending in front of each orifice 11. The flowing or aspiration at the level of said exit 15 then returns the fluid inside the circuit 10 towards the means for putting into circulation 9.

It should be noted that this return of the fluid can occur directly inside the circuit 10, towards recycling means or through filtering means 16 located in the lower portion, under said cavity 12. In fact, the outlets 15 thus pass through the lower wall of said cavity 12, so as to guide the fluid towards said filtering means 16 located below.

In addition, as visible in FIG 2, said filtering means 16 can be in the form of a permeable membrane, namely formed of fibers, foam or a woven material the separation of which permits to recover the ear wax particles, whether liquefied or not, as well as the dust and dirt, while letting pass the liquid. The latter is then redirected towards the means for putting into circulation 9, or it can be returned into the circuit 10.

According to the embodiment visible in the figures, in particular in FIG 3, said space 3 comprises in the lower portion a tank 17 for storing said liquid. Therefore, the circuit 10 starts from said tank 17 in order to aspire the liquid until a pump forming the means for putting into circulation 9, which returns the liquid to each pipe 13. The liquid then flows on the bottom of the cavity 12, along the fins 14, until the outlet 15, or it is filtered before returning to said tank 17.

FIG 6 schematically shows by means of arrows the concentric flow direction of the fluid towards the two outlets 15.

According to a preferred embodiment, said tank 17 can be formed by a removable cartridge 170, as shown in FIGS. 7 and 8.

Said cartridge 170 has a cylindrical shape, a diameter equal to or lower than the diameter of said space 3, so as to permit its insertion with or without backlash. Moreover, the height of the cartridge 170 is smaller than the depth of said space 3, so as to permit its complete insertion inside and to permit the positioning of said dome support 300, ensuring a tight closing.

It should be noted that said space 3 can then comprise one or several annular seals at the level of its inner wall, so as to ensure the tightness with the vertical peripheral wall of said cartridge 170, with said dome support 300, and the lower portion of said space 3 that, in turn, constitutes then at least partially the tank 17.

Advantageously, said cartridge 170 is subdivided internally into several compartments.

In the first place, the cartridge 170 comprises compartments 172 for storing said cleaning fluid. In fact, when the cartridge 170 is used for the first time, these storage compartments 172 are closed and filled.

In particular, the cartridge 170 comprises two storage compartments 172 that are in the form of portions of the inner volume of the cylinder constituting said cartridge 170. In fact, these two compartments 172 are each delimited by the outer peripheral wall 173 and by two substantially radial or radial walls 174, the latter intersecting at a ridge 175 extending parallel to the central axis of said cylinder, in the vicinity of the latter.

Thus, these radial walls 174 also determine two further compartments 176 for recycling the fluid after use. Preferably, these two recycling compartments 176 are connected to each other at the level of said central axis, forming a horizontal cross-section comparable to an hour glass. This specific shape ensures the filling with recycled fluid to the same height in these two compartments 176.

In this respect, the filling of the latter occurs through two recycling orifices 177 provided for in the upper face 178 of the cartridge 170.

Furthermore, in the lower face 179, two orifices 180 are provided for at the level of the storage compartments 172. These orifices 180 are closed by protection caps 1800 aimed at being perforated at the moment of placing the cartridge 170 inside the space 3. To this end, perforating pawls can be positioned protruding on the bottom of said space 3, so as to perforate said protection caps 1800 and at the same time to serve as a guide pin for perfectly positioning the cartridge 170 inside the space 3.

In addition, in the upper face 178, holes 181 are provided for at the level of said storage compartments 172. These holes 181 are closed by a tongue 182 designed removable or that can be perforated. Once removed or perforated, said tongue 182 lets the air enter into each storage compartment 172 and the liquid can then flow through the orifices 180, filling the bottom of the space 3, until it arrives flush with the cartridge 170.

According to an additional feature, said cartridge 170 can comprise two central channels 183 having a cylindrical shape passing internally through the cylinder from the upper face 178 to the lower face 179 and ending outside at the level reciprocally of upper holes 184 provided for in the upper face 178 and of lower holes 185 provided for in the lower face 179.

These channels 183 then form a portion of the circuit, through which the fluid transits during the cleaning, from the recesses 4 located in front of said upper holes 184 during the fluid-cleaning and circulating step.

In particular, the lower holes 185 can have, in the thickness of the wall of the lower face 179 and/or partially in the thickness of the walls of said channels 183, a widening for receiving the filtering means 16. In particular, the latter are then in the form of a circular filter 160. Such filters can be maintained in place through annular rings 161, which insert into said widening.

Furthermore, these filters 160 and these rings 161 can be maintained in place through a bottom plate 186. The latter can be fixed to the bottom of the cartridge 170 in a removable or non-removable way. Said plate 186 also has the aforementioned orifices and holes in order to permit the circulation of the fluid.

Advantageously, said cartridge 170 can have a symmetry with respect to its central axis, facilitating its positioning without any particular direction, thanks to said guiding pins formed by the protrusions of the bottom of the space 3.

From what has been set forth above, one understands that the fluid can circulate from the storage compartments 172, through channels 183 or to the recycling compartments 176.

To this end, said space 3 is closed after positioning the cartridge 170 by the tight-closing dome support 300. The latter has a cross-section complementary to the cross-section of the space 3, so as to insert into same in the upper portion. After insertion, said dome support 300 is movable in rotation according to the central axis of said space 3. It is then possible to rotate it clockwise or inversely.

It should be noted that in order to facilitate these rotations, but also the insertion or extraction, said dome support 300 can comprise gripping means 350 permitting the user to take it between his fingers.

First of all, in a first position, the dome support 300 can be inserted or removed. In particular, during its insertion, the resting face permits to push on cartridge 170 and to perforate the protection caps 1800.

In another position, after a rotation according to a determined angle, the dome support 300 is locked in cleaning position. Therefore, the recesses 4 and the orifices 11 are in front of the upper holes 184 of the cartridge 170, ensuring the circulation of the fluid during the cleaning.

In a third recycling position, the rotation of the dome support 300 according to another predefined angle, brings said recesses 4 and orifices 11 in front of the recycling orifices 177 of the recycling compartments 176. The system can then be emptied of all its fluid.

It should be noted that in cleaning or recycling positions, said dome support 300 is then locked vertically, i.e. it cannot be extracted, as in the first position.

To this end, the peripheral edge of said dome support 300 can have grooves 301 aimed at cooperating with complementary protrusions provided for internally at the periphery of the high wall of said space 3.

According to the preferred embodiment, said dome support 300 can be formed of an upper portion 302 and a lower portion 303. The latter are then fixed together in a removable or non-removable way, namely by means of clips.

Between these two portions 302 and 303 can be positioned a seal 304, in order to ensure the tightness.

In addition, said dome support 300 can comprise a rod 305 serving as a support at the distal end of the ear mold of the earpieces 101 that must be cleaned. In fact, this support rod 305 ensures the maintaining of said end above the fluid during the cleaning, so that it is not immersed directly in it and that it is only <<lapped against>> without being immersed.

In particular, said support rod 305 has two through-holes each provided with a <<basket>> 306 on which rests the earpiece 101, in particular the standard or made-at-measure ear mold of the latter.

This rod 305 is then sandwiched during the fastening of the portions 302 and 303, an opening having a complementary shape being provided for at the level of said seal 304. It should then be noted that the rod 305 can have a flat elongated, approximately oval, shape.

In addition, the lower portion 303 integrates a portion of the cleaning circuit of said fluid. In fact, this lower portion 303 is hollow, so as to provide in it for grooves inside which the fluid will flow during the cleaning.

According to the preferred, but in no way restrictive, scheme shown in FIG 9, an opening 307 is provided for at the periphery. It is connected to a bifurcation connecting two symmetrical groves 308 that each end in front of a wall 309 having the shape of an arc of a circle, preferably a semi-circle. During the flowing of the fluid, it is biased on both sides. However, a larger amount of fluid is directed to one side of the wall 309 (downwards in FIG 9), because of the direction of the grove groove 308. Then, at the level of each end of each wall 309, a stop 310 is provided for at right angles. The fluid biased by the wall 309 is then returned inwardly.

It should be noted that in the circular space on the other side of the wall 309 an outlet 311 (coinciding with the outlet 15) is provided for.

The fluid guided by the preceding elements creates the vortex in the circular space, which vortex will brush the distal end of the earpiece 101. In particular, the dissymmetry resulting from the direction of each grove groove 308 and from the wall having the shape of a semi-circle 309, improves the effect of rotation in the flow maintaining the vortex or this whirl, the aspiration of which occurs through said outlet 311.

It should be noted that said dome support 300 can then have seals 313 in order to ensure the tightness with said cartridge 170, in particular at the level of the outlets 311 with the upper holes 184 or the recycling orifices 177 or the holes 181.

In fact, the circular space corresponds to the cavity 12. Therefore, the directing means 14, which are in the form of protrusions, veins or groves, can be provided for at the level of said circular space, changing the flow of the fluid and, hence, improving the vortex effect.

Furthermore, on the other side of the circular space, in front of the wall 309, is provided for a funnel 312 ensuring the blowing of hot air. The funnel 312 is designed convergent from an open end at the periphery of the lower portion 303 to an opposite end ending in the circular space.

In addition, this funnel-shape reduces the amount of fluid that could not be aspired by the vortex and the outlet 311. This particular funnel-shape also creates a venturi effect that accelerates the hot air being blown.

In this respect, during the putting into circulation of said fluid, the latter can be heated by adapted means or in contact with the room temperature or air heated by said heating means 5.

In this respect, as can be seen in FIG 5, said cleaning device 2 comprises means 5 for heating air and means 6 for putting the heated air into circulation in a circuit 7 ending inside said space 3.

It should be noted that said heating means 5 can be in the form of an electric heating, such as resistors 50 in contact with the air to be heated and then forming a heat exchanger.

In addition, said means for putting into circulation can be in the form of a pump or a ventilator, forming means for blowing heated air at an end of said circuit 1 and aspiring air from the opposite end. In particular, said circuit 7 is open at the level of the space 3, through opening 8 for blowing and taking up air, so that the blowing propels the heated air into said space 3, while the aspiration permits the return of the air towards said means for putting into circulation 6. Therefore, said space 3 can be designed tight, except for said openings 8, in closed position of the enclosure of the device 2.

In addition, the temperature of heating of the air by heating means 5 is capable of drying the atmosphere inside the enclosure and the aids, in particular the ear molds of the earpieces 101.

More specifically, the heating temperature of the heating means 4 is foreseen so as not to deteriorate the electronic components of said earpiece 101. The lowest temperature permitting heating and drying may be of 40 degrees Celsius. The highest temperature may be of 60 degrees Celsius, avoiding damaging the electronic components.

Advantageously, during the operation of the device 2 according to the invention, the liquid is put into circulation as evoked above, for a determined period of time sufficient to completely clean the ear mold of each earpiece 101. A cleaning time may take several minutes, even several tens of minutes, namely and approximately 20 minutes.

A period of time is then necessary for draining, i.e. the flowing out of the fluid or its aspiration into said tank 17. Then only particles of the liquid and room moisture remain at the level of the cavity 12.

During and/or after this cleaning by humidifying part of the ear mold of each earpiece 101, then this flowing-out phase, air is heated and put into circulation in order to dry the earpieces 101. A drying cycle may take several minutes, even several tens of minutes, namely and approximately 20 minutes.

Thus, this drying step ensures the complete removal of all the moisture or presence of the slightest particle of fluid or liquid that would remain due to the cleaning, avoiding any risk of short-circuiting at the level of the electronics at the moment of the switching-on or restarting of the aid 1.

In addition, the enclosure can provide a circulation of blown hot air, namely through the space 3 through recesses 4, or through openings provided for inside said enclosure. Therefore, a natural flow of less hot air can occur from the bottom to the top of the enclosure, ensuring that no room moisture enters into contact with the aid 1, except with the end of the ear molds of each earpiece 101.

According to particular embodiments, means for controlling the heating, the putting into circulation of the air and the liquid, the duration of the cleaning, can be added. They permit to define cleaning cycles in an automatic or parameterable way.

Thus, the present invention ensures an improved cleaning by humidifying the fouled portion of the ear mold of each earpiece 101, ensuring a liquefaction of the ear wax and its aspiration as close as possible to each earpiece 101, without deteriorating the latter.

What is claimed:

1. A device for cleaning at least one medical hearing aid, said hearing aid being comprised of an earpiece formed by an ear mold and shaped to be inserted into a person's auditory meatus, said device for cleaning comprising:
    a box;
    a housing defining a space within said box, said space for receiving said earpiece;
    a closing plate removably contained in said housing, said closing plate having an upper plate portion and a lower plate portion;
    a recess being shaped so as to receive said ear mold, said recess having an upper recess portion and a lower recess portion, said upper plate portion housing said upper recess portion, said recess comprising an orifice in said lower recess portion, said orifice being shaped so as to receive a distal end of said ear mold;
    a cavity plate removably contained in said housing, said cavity plate defining a cavity within said space and below said lower plate portion, said lower recess portion of said recess protruding into said cavity, said orifice being positioned in said cavity,
    said cavity plate being comprised of an outlet aligned with said orifice, and means for directing liquid towards said outlet so as to lap liquid against said distal end of said ear mold when said ear mold is placed in said recess; and
    means for putting a liquid into circulation, being in fluid connection with said orifice and having a nozzle tip in said cavity.

2. The device for cleaning, according to claim 1, wherein said means for directing liquid are comprised of at least one of a group consisting of protrusions, veins and grooves.

3. The device for cleaning, according to claim 1, further comprising:
    a means for heating said space through circulation of heated air, said means for heating in fluid connection with said cavity.

4. The device for cleaning, according to claim 1, further comprising:
    filtering means located under said cavity plate, said filtering means being in fluid connection with said cavity.

5. The device for cleaning, according to claim 4, wherein said filtering means are comprised of a permeable membrane formed by at least one of a group consisting of fibers, foam and a woven material.

6. The device for cleaning, according to claim 1, further comprising:
    a cartridge with a cylindrical body inserted in said space, said cartridge having a top end and a bottom end, said cartridge being subdivided internally into a plurality of compartments, each compartment being defined by a peripheral wall of said cylindrical body and radial walls, said cavity plate being formed on said top end of said cartridge,
    wherein each compartment is in fluid connection with said cavity, said means for putting a liquid into circulation being contained in said box so as to circulate liquid through at least one compartment, said nozzle tip, said outlet, said cavity, said orifice, said cavity again, and back to said cartridge.

7. The device for cleaning, according to claim 6,
    wherein said plurality of compartments is comprised of storage compartments and recycling compartments,
    wherein each storage compartment has a lower storage face and an upper storage face, said upper storage face aligned with said top end of said cartridge, said lower storage face having a storage orifice and a protection cap covering said storage orifice, said upper storage face having a hole,
    wherein each recycling compartment has a lower recycling face and an upper recycling face, said upper recycling face aligned with said top end of said cartridge, said upper recycling face having two recycling orifices.

8. The device for cleaning, according to claim 7, wherein said cartridge further comprises two central channels each central channel having a cylindrical tubular member passing internally through said cylindrical body of said cartridge from said top end to said bottom end,
    wherein said top end of said cartridge has upper holes, and
    wherein said bottom end of said cartridge has lower holes, each central channel extending from a respective upper hole to a corresponding lower hole.

9. The device for cleaning, according to claim 1, wherein said closing plate has a cross-section complementary to a cross-section of said housing defining said space, said closing plate being rotatably mounted within said space.

10. The device for cleaning, according to claim 9, wherein said lower plate portion of said closing plate is comprised of a lower plate with a plurality of grooves, and an opening being provided for at a periphery of said lower plate, said opening and grooves being in fluid connection with said nozzle tip, said outlet, and said orifice, each groove having an arc shaped wall, stop members at ends of the wall, and an exit at said periphery of said lower plate, so as to direct said liquid around the wall toward the stop members and so as to build liquid levels at the stop members before flowing through said exit.

11. The device for cleaning, according to claim 1, wherein said recess is comprised of a flexible and elastic material.

12. The device for cleaning, according to claim 1, wherein said liquid is selected from a group consisting of a cleaning fluid and a disinfecting fluid.

\* \* \* \* \*